United States Patent [19]

Fraioli

[11] Patent Number: 4,477,541

[45] Date of Patent: Oct. 16, 1984

[54] SOLID ELECTROLYTE STRUCTURE

[75] Inventor: Anthony V. Fraioli, Hawthorn Woods, Ill.

[73] Assignee: The United States of America as represented by the United States Department of Energy, Washington, D.C.

[21] Appl. No.: 452,361

[22] Filed: Dec. 22, 1982

[51] Int. Cl.³ .............................................. H01M 8/10
[52] U.S. Cl. .................................... 429/33; 204/277; 204/421; 429/191; 429/30
[58] Field of Search ............... 204/421, 422, 423, 424, 204/425, 426, 427, 428, 429, 277; 423/592, 600, 605; 429/191, 30, 31, 32, 33

[56] References Cited

U.S. PATENT DOCUMENTS

| | | | |
|---|---|---|---|
| 3,300,344 | 1/1967 | Bray et al. | 136/86 |
| 3,410,728 | 11/1968 | Fullman et al. | 136/86 |
| 3,464,861 | 9/1969 | Williams et al. | 429/30 |
| 3,684,578 | 8/1972 | Makishima et al. | 136/86 |
| 3,839,181 | 10/1974 | Degveldre et al. | 423/600 |
| 4,024,036 | 5/1977 | Nakamura et al. | 204/129 |
| 4,067,792 | 1/1978 | Semkina et al. | 204/421 |
| 4,070,529 | 1/1978 | Delmas et al. | 204/421 |
| 4,197,171 | 4/1980 | Dunn | 204/16 |
| 4,277,360 | 7/1981 | Mellors et al. | 252/182.1 |
| 4,329,403 | 5/1982 | Baker | 429/46 |
| 4,333,846 | 6/1982 | Lee et al. | 423/600 |

FOREIGN PATENT DOCUMENTS

| | | | |
|---|---|---|---|
| 2723872 | 12/1977 | Fed. Rep. of Germany | 429/30 |
| 2755650 | 4/1978 | Fed. Rep. of Germany | 429/30 |
| 49-113790 | 10/1974 | Japan | 423/600 |
| 56-45829 | 4/1981 | Japan | 423/605 |

OTHER PUBLICATIONS

McKenzie, Minerlogical Magazine 28, 493–502, 1971.
Fraioli, IRE Transactions on Component Parts, CP-5, No. 2, Jun. 1958.
Vogel et al., Program and Abstracts, National Fuel Cell Seminar, Jun. 1981, 127–129.
Wagner, Jr., Mat. Res. Bull. 15, pp. 1697–1701, 1980.
Jow et al., J. Electrochem Soc. 126, 1963, 1979 (1979).
Stoneham et al., Mat. Res. Bull. 14, pp. 661–666 (1979).
Turner et al., Science 212, May 29, 1981, pp. 1024–1027.

Primary Examiner—T. Tung
Assistant Examiner—Terryence Chapman
Attorney, Agent, or Firm—William Lohff; Hugh W. Glenn; Michael F. Esposito

[57] ABSTRACT

A solid electrolyte structure for fuel cells and other electrochemical devices providing oxygen ion transfer by a multiplicity of exposed internal surfaces made of a composition containing an oxide of a multivalent transition metal and forming small pore-like passages sized to permit oxygen ion transfer while limiting the transfer of oxygen gas.

14 Claims, 4 Drawing Figures

SOLID ELECTROLYTE STRUCTURE

CONTRACTUAL ORIGIN OF THE INVENTION

The U.S. Government has rights in this invention pursuant to Contract No. W-31-109-ENG-38 between the U.S. Department of Energy and the University of Chicago representing Argonne National Laboratory.

BACKGROUND OF THE INVENTION

This invention relates to oxygen ion conducting electrolytes having enhanced oxygen ion transfer, and to electrochemical devices having an oxygen-rich electrode and an oxygen-deficient electrode in association with the inventive electrolyte, and more particularly to electrochemical devices including fuel cells having a multiplicity of internally exposed, oxygen ion transfer surfaces within an electrolyte zone to improve the oxygen ion transfer rate between the electrodes. More specifically, the invention relates to solid electrolyte fuel cells operable at reduced temperatures in the order of about 200°–800° C. and having a multiplicity of internal passages or pores to enhance oxygen ion transfer. The pores are sized to limit gas transfer but permit oxygen ion transfer along the surfaces of pores in a lateral direction from the oxygen electrode or cathode towards the fuel electrode or anode.

Typical solid electrolyte fuel cells utilize a porous fuel anode, a porous oxygen cathode and a crystalline electrolyte. Their operating temperatures are usually about 1000° C. in order that an adequate quantity of oxygen ions are transferred per unit time across an oxygen ion transfer gradient in the electrolyte by "hopping" between oxygen vacancies within the crystal structure. Usually, the electrodes have good electronic conductivity while the electrolyte has poor electronic but good ionic conductivity. In general, these solid electrolyte fuel cells have been identified with problems in performance and natural stability associated with the high operating temperatures.

A number of developments have been carried out to reduce the high operating temperatures and other problems associated with these solid electrolyte fuel cells. In U.S. Pat. No. 4,024,036 a heteropoly acid represented by the formula

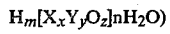

$$H_m[X_xY_yO_z]nH_2O)$$

has been disclosed as a proton permselective electrolyte. In the above formula, X includes a variety of metals including transition metals while Y is a transition metal but not the same as X.

In U.S. Pat. No. 3,300,344, a fuel cell is disclosed with a solid gas-impervious electrolyte compound of $ZrO_2$ and $Y_2O_3$ which has oxide vacancies for transfer of the oxide ion through the solid electrolyte, and with porous electrodes. For the cathode, a porous nonconductive matrix of the electrolyte composition is loaded with manganese oxide to improve electrical conductivity.

Other disclosures of interest may be found in U.S. Pat. No. 3,684,578; U.S. Pat No. 4,277,360, U.S. Pat No. 4,197,171 and U.S. Pat. No. 3,410,728.

At lower temperatures in the order of 600°–800° C., molten carbonate fuel cells with molten carbonates melting in the range of about 400°–700° C. are preferred over solid electrolyte fuel cells to achieve acceptable output current levels. The transfer of oxidant ions in the molten carbonate fuel cells is achieved by the initial formation of oxygen ions followed by their combination with carbon dioxide to form carbonate ions as a means of transferring the oxygen ions across the electrolyte. An initial conditioning of the cell is normally carried out at about 650° C. for about one to two hundred hours (and usually about 50 hrs) to achieve normal performance levels associated with a plateau on the performance curve. After the conditioning period, the operation of the cell tends to be limited by the rate at which carbonate ions form. In general, the molten carbonate fuel cells have problems associated with the initial conditioning period, the maintenance of the molten carbonate, and corrosion of cell components by the molten carbonate.

One object of this invention is an oxygen transport electrolyte with enhanced oxygen ion transfer properties. A second object of this invention is an electrochemical device with a solid electrolyte structure providing oxygen ion transfer and operable at temperatures below about 1000° C. A third object of the invention is a molten carbonate fuel cell operable at temperatures below about 800° C. Another object of the invention is a molten carbonate fuel cell with an improved oxygen ion transfer rate. Yet another object of the invention is a fuel cell with a solid electrolyte. Still another object of the invention is a molten carbonate fuel cell operable at temperatures below about 800° C. with reduced conditioning requirements to achieve plateau operating performance. An additional object of the invention is a solid electrolyte fuel cell operating in the absence of molten carbonate yet operable at temperatures below 1000° C. and preferably below about 800° C. A further object of the invention is a solid electrolyte fuel cell with desirable characteristics of oxygen ion transfer within a solid electrolyte structure. A further object of the invention is an electrochemical cell operating with a solid electrolyte and an oxygen-rich electrode and a second, oxygen-deficient electrode for gas sensing and electrolytic oxygen-pumping applications.

SUMMARY OF THE INVENTION

Briefly, the invention is directed to a solid electrolyte structure for electrochemical cells and to an electrochemical device having an oxygen electrode, a fuel electrode, and ion transfer means for accepting oxygen ions from the oxygen electrode, the ion transfer means including a solid electrolyte structure having a multiplicity of exposed internal surfaces for oxygen ion transfer. It has been found that this structure in a molten carbonate fuel cell with an adjacent source of transition metal for the electrolyte provides an improved oxygen ion tranfer and reduces the initial conditioning period substantially. This may in part be due to the recognition by the inventor that the extensive initial conditioning period may have caused a migration of corrosion products with metal ions from the cathode and cell housing to the electrolyte in previous molten carbonate fuel cells. With the improved oxygen ion transfer performance provided by the solid electrolyte of this invention, the use of the electroltye as the primary electrolyte in a solid electrolyte fuel cell will permit the operation of the cell at temperatures below about 1000° C. and at temperatures of about 800° C. and below.

Advantageously, the solid electrolyte structure internally has a multiplicity of small, open pores to provide the internal surfaces with the pores being sized to accommodate the passage of oxygen ions but being generally impermeable to the passage of molecular gases and particularly hydrogen and oxygen. Advantageously, the structure further provides a composition around the pores composed of an oxide of a multivalent metal capable of adsorbing and desorbing and readsorbing oxygen ions to thereby serve as an oxygen ion transfer agent while having insulating properties with respect to electron transfer. In one embodiment of a solid electrolyte fuel cell, the electrolyte is predominantly composed of manganese oxides in the form of $MnO_2$ and/or $Mn_3O_4$ with the multiplicity of small, open pores being inherently formed in the structure. In the operation of the cell, the formation of near $Mn_3O_4$ near the anode provides at least a portion of the insulating properties with respect to electronic transfer in this embodiment.

In the operation of an electrochemical device of the invention, oxygen ion conduction is provided along internal pore surfaces of the solid electrolyte. The oxygen ion conduction may be characterized as a surface-film of adsorbed oxygen ions maintained by an oxygen ion concentration gradient provided by an excess of oxygen ions at one extremity of the electrolyte, a deficiency at the other, and with a nominal absence of both fuel or oxidant gases over the interior portions of the electrolyte surfaces. While particularly useful for fuel cells, the application of the solid electrolyte structure of this invention particularly as characterized by a multiplicity of small, open pores is not restricted to fuel cell structures, but may be incorporated into oxygen sensor systems with electrode means designed for automatic carburetion and emission control in internal combustion engines, industrial combustion control, and electrolytic oxygen pumps which regulate or regenerate oxygen partial pressures in controlled atmospheres, and to other applications known to those skilled in the art.

DETAILED DESCRIPTION OF THE INVENTION

Figure 1:
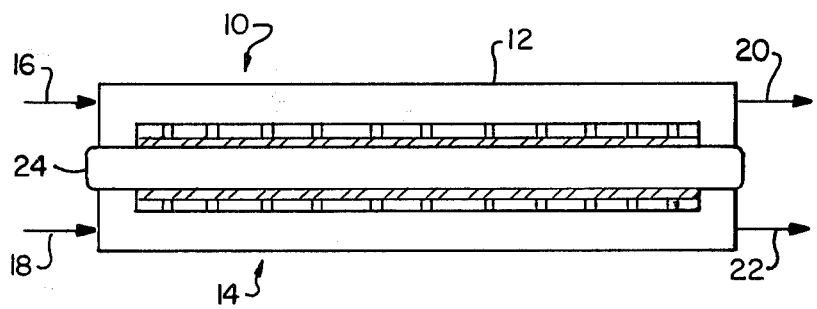
FIG. 1 is a side view of a solid electrolyte fuel cell illustrating one embodiment of the invention.

The electrolyte of the invention may be utilized as a component for use with a pair of electrodes in an oxygen sensor or electrolytic cell, or in combination with a pair of electrodes as in a fuel cell. Advantageously, the electrolyte comprises an elongated layer composed of a multiplicity of small, open pores sized to permit oxygen ion transfer but limit oxygen and hydrogen gas. Preferably, the layer has a density of about 2-5 gm/cc and is essentially gas-tight and is structurally and chemically stable at the elevated temperature. Advantageously, the inventive cell comprises one oxygen-rich electrode for generating oxygen ions, ion transfer means including a solid electrolyte structure for accepting oxygen ions formed on the electrode, and a second oxygen-deficient (or fuel) electrode as a means for withdrawing the oxygen ions from the electrolyte. Means are provided for introducing an oxygen-containing gas to the oxygen electrode and for introducing an oxygen-deficient or reducing gas to the second electrode.

The ion transfer means includes a solid electrolyte structure with enhanced oyxgen ion transfer performance and restricted oxygen gas transfer. In an embodiment in a molten carbonate fuel cell, an electrolyte structure of ceramic composition is provided in combination with an adjacent source of nickel as the transition metal. During an initial heating of the cell, the transition metal-ion migrates to the solid electrolyte structure and provides enhanced surfaces exposed internally in the structure. With the molten carbonate providing a barrier to oxygen gas transfer, the electrolyte structure is primarily characterized by internal passages having an enhanced surface composition composed of a transition metal oxide.

The term "solid electrolyte structure" is intended to refer to a solid structure with the extensive internal exposed surfaces providing enhanced oxygen ion transfer and particularly a pore structure as described herein. It may provide an oxygen ion transfer system in conjunction with an adjacent electrolyte as in a molten carbonate fuel cell or as the primary electrolyte as in a solid electrolyte fuel cell, or be used in an oxygen sensing or pumping device. In the inventive electrochemical device, the solid electrolyte structure preferably is predominantly composed of a multiplicity of small, open pores sized to permit the passage of oxygen ions but substantially impermeable to the passage of oxygen gas. Advantageously, the composition around the pores is composed of an oxide of at least one multivalent metal capable of adsorbing and desorbing oxygen ions to serve as an oxygen ion surface-transfer agent.

The solid electrolyte structure preferably adjoins the oxygen electrode and serves to provide active internal surfaces for the transfer of oxygen ions laterally away from the electrode. The solid electrolyte structure may be used with a separate electrolyte as in a molten carbonate fuel cell or may serve as the primary electrolyte and extend between the electrodes as in a solid electrolyte fuel cell.

In general, the pores are sized below about $1 \times 10^4$ Å and preferably about 5–100 Å. These pores extend in a lateral direction from the oxygen electrode. In a fuel cell, the pores may extend substantially across the electrolyte although the oxygen ions are consumed as they react with the hydrogen ions (or hydrogen gas) at or near the anode. The pores may extend as continuous pores or may be formed of a series of individual pores forming a twisting path across the structure. As in several forms of manganese oxide, the pores may be an inherent part of the structure. In some instances, the structure may be formed of particles of a material compacted together to form the pore structure. Also, the pores may be formed by compacting dense inorganic powders with contiguous decomposable fiber networks which are removed by heating the material to an elevated temperature.

Suitably, the solid electrolyte structure may be composed of a metallic oxide containing one or more multivalent metal ions and having the desired porosity. Ceramic oxides provide many advantages, particularly those containing one or more of the transition metal ions and particularly those capable of variable valences of 3 and above. The structure may contain other components such as alkaline metal ions in addition to the multivalent metallic oxide as the oxygen ion transfer agent or it may be composed predominantly of the desired metallic oxide.

Suitable oxides of multivalent metals include the transition metals of Periods 4, 5 and 6 of the Periodic Table such as manganese, cobalt, nickel, copper, iron, zinc, vanadium, chromium, titanium, molybdenum, ruthenium, rhodium, palladium, iridium, rhenium, osmium and platinum, and the like and nontransition metals including the stably-trivalent Group 3A and 4A metals which are capable of forming a substrate for the incorporation of variably-valent oxides and primarily aluminum and tin. Preferably, the transition metal is manganese, nickel, titanium, vanadium, chromium, or molybdenum. Other univalent metal cations such as Li, K, Rb and Cs may also be present. In general, the oxide may be expressed as $$T_a X_b O_c$$

wherein T is a transition metal, X is the transition metal, Al, Sn, and an alkali metal such as Li, K, Rb, Cs, and the integers a, b, and c represent the number of atoms to balance the formula. Illustrations of these oxides include the transition metal oxides where X equals T as in $MnO_2$, $NiO$, $CoO$, $CuO$, $Fe_2O_3$, $ZnO$, $V_2O_5$, $TiO_2$, $MoO_3$, $RuO_2$, $PdO$, $IrO_2$, $Re_2O_7$, $OsO_2$, $PtO_2$ and the like. Where X is not a transition metal, illustrations include $MnAl_2O_5$, $NiAl_2O_4$, $CoAl_2O_4$, $CuAl_2O_4$, $FeAlO_3$, $ZnAl_2O_4$, $VAlO_4$, $TiAl_2O_5$, $MoAl_2O_6$, $RuAl_2O_5$, $PdAl_2O_4$, $IrAl_2O_5$, $ReAlO_5$, $OsAl_2O_5$, $PtAl_2O_5$, $MnSnO_4$, $MoSnO_5$, $LiMn_8O_{16}$, $KMn_8O_{16}$ and the like.

The structure forming the internal surface includes an oxygen ion transfer agent which operates under an oxygen ion gradient source of at or near the cathode and depleted towards the anode. The oxygen-ion transfer agent is composed of a multivalent transition metal compound in which the transition metal is capable of changing valences, or alternatively, is capable of "hole formation" at or near its resident position in the lattice.

In prior art molten carbonate cells, migration of nickel or other metal during the conditioning process may transfer a metal to the electrolyte structure. However, this may limit the operation of the cell since hydrogen reaction with the transition metal may form undesirable deposits. Previously, manganese dioxide has been utilized in low temperature batteries in the form of a wet paste adjacent a carbon electrode and has served as a source of hydroxide ions which have been transferred within the wet mixture. In the process, $MnO_2$ is reduced in oxygen content and converted to $Mn_3O_4$.

In the molten carbonate fuel cell of this invention the rate is reproducibly accelerated by the incorporation of a reactive source of transition metal ions (in the form of a thin layer of partially-reduced spinel) at the cathode-tile interface. Thus the transfer agent is incorporated into the tile structure without the extensive conditioning required in the prior art cell. For solid electrolyte fuel cells, the solid electrolyte provides the structure in a form with improved oxygen ion transfer agent to permit the operation of the cell at a temperature below about 1000° C. Advantageously, the structure has internal passages or channels with surfaces of the desired composition and sized to permit the transfer of labile oxygen ions weakly adsorbed on the surface while being limited and preferably impermeable to the diffusional transfer of oxidant or fuel gases as molecular species in the free volume of the channels or particle interstices of the "solid" electrolyte. For solid electrolyte fuel cells, the solid electrolyte structure of the invention provides an increased oxygen ion transfer rate permitting operation of the cell at temperatures below about 1000° C. and advantageously about 200°–800° C.

In the oxygen ion transfer, the multivalent transition metal ion acts to accommodate the residence of an oxygen ion concentration gradient on at least a portion of the solid electrolyte surface structure. As an illustration, the oxides of manganese may serve as the composition for an electrolyte of a solid electrolyte fuel cell. At the cathode, $MnO_2$ may be the predominant composition, while $Mn_3O_4$ may be present within the structure a distance from the cathode. Further, both $MnO_2$ and $Mn_3O_4$ are advantageous since their structures include pores of suitable size, $Mn_3O_4$ is not reduced to metallic manganese by exposure to hydrogen at 650° C., and $Mn_3O_4$ provides electron insulating properties to the composition.

Figure 4:
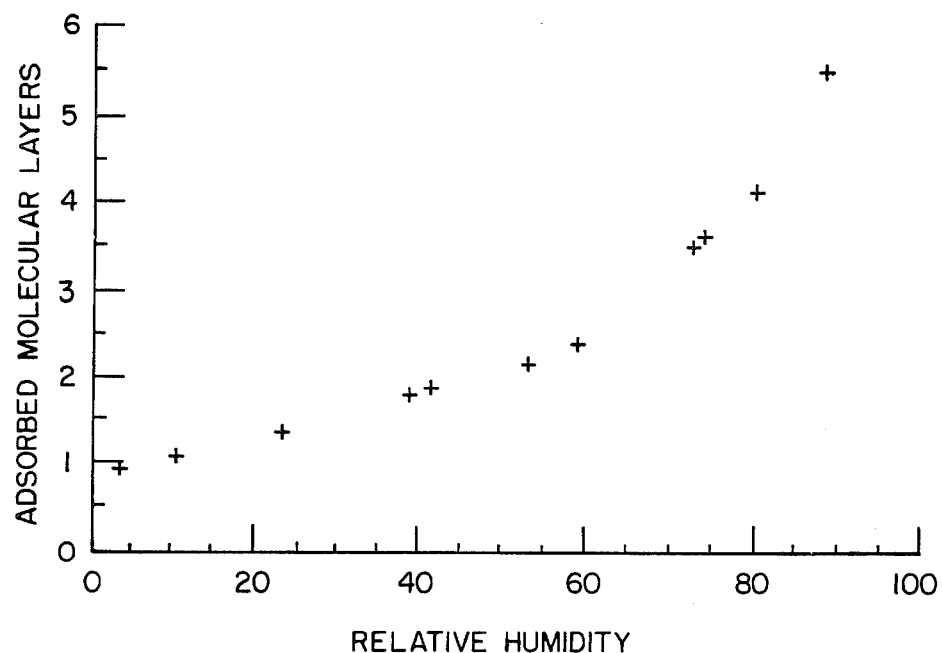
FIG. 4 is a graph of water adsorption data for a sample of manganese dioxide.

The oxides of manganese were shown to have an additionally advantageous characteristic in providing large areas of inner-channel surface which offer a monoenergetic adsorption potential to adsorbed species along the surface of the channel. FIG. 4 is a graph based on test data which show reduced adsorption isotherm for water vapor on a powdered aggregate sample of 50 $m^2/g$ synthetic cryptomelane ($KMn_8O_{16}$ $nH_2O$), activated at 125° C. with adsorption carried out at 20° C. The FIG. 4 follows the Type III adsorption isotherm characteristic of weakly-bound adsorbate-to-adsorbent coupling. The lower cusp extending over the formation range of the first physically adsorbed layer is indicative of adsorbate behavior as a two-dimensional gas on the surface prior to monolayer formation. This requires a monoenergetic surface characteristic inherent in the adsorbent substrate. It thus provides the fuel cell of this invention with an improved oxygen-ion conduction means not requiring high activation energies for site-to-site oxygen ion transfer, with an improved (decreased) polarization voltage drop across the electrolyte at substantially-reduced operating temperatures than are required for the operation of state-of-the-art yttria-stabilized zirconia solid electrolyte fuel cells.

With further reference to the drawings, FIG. 1 is an illustration of a representative solid electrolyte fuel cell with the components mounted vertically in a stack array. Details regarding the electrical interconnections and gas manifolding for the cell are conventional and not illustrated. For the cell 10, cathode and anode housings 12 and 14 house the electrodes and are typically constructed of stainless steel. An oxygen containing gas is introduced into the cathode housing 12 by line 16 while line 18 serves as a means for introducing hydrogen as a gaseous fuel to the anode housing 14. Lines 20 and 22 serve as the means for removing the spent oxidant and fuel, respectively. Cell member 24 constitutes the molten carbonate electrolyte or a solid oxide electrolyte as described herein with opposite surfaces adjacent the electrodes. The lips of the anode and cathode cell housings are aluminized in the seal areas to provide rectifying contact and blockage of short-circuiting currents between cell housings through the electrolyte.

The following examples are provided to illustrate some embodiments of the invention and are not intended to be limiting with respect to the scope of the invention.

EXAMPLE I

Figure 3:
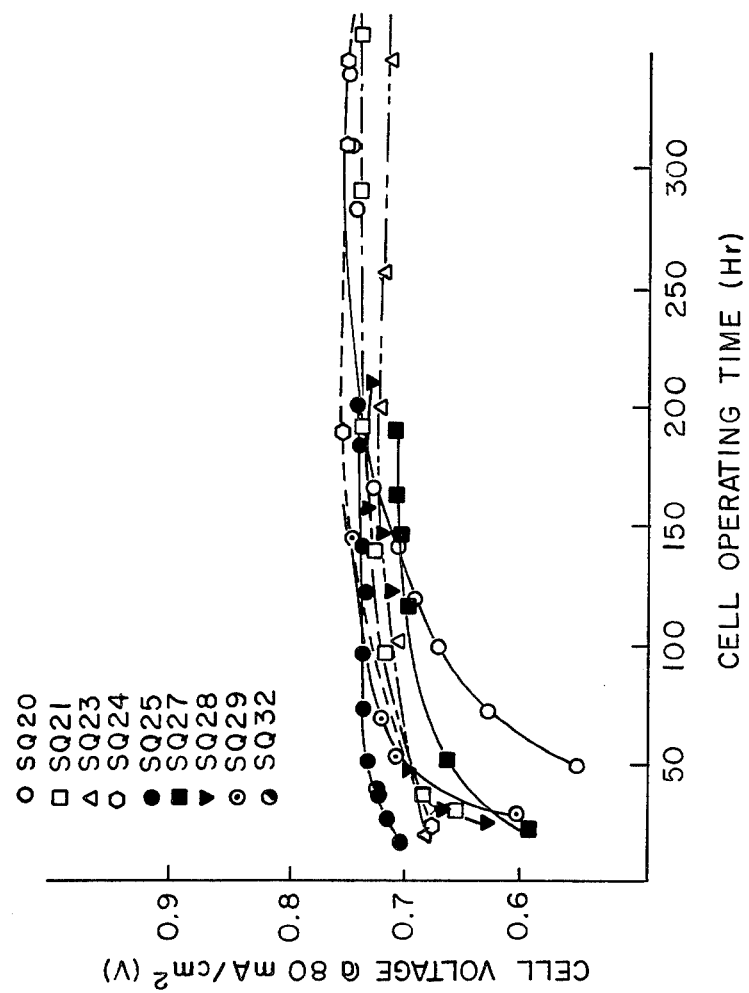
FIG. 3 is a graph of performance data for several molten carbonate fuel cells.

In the preparation of a molten carbonate fuel cell whose performance is illustrated in FIG. 3, a surface of a preoxidized nickel cathode was spray-coated with an aqueous slurry of Ni/NiAl$_2$O$_4$. After drying, the coating weighed approximately 0.88 g.

In the preparation of a nickel spinel, Ni/NiAl$_2$O$_4$ was prepared from high surface gamma-alumina. About 294 g of Al$_2$O$_3$ was combined with about 839 g of Ni(NO$_3$)$_2$ and about 480 g of water to form a slurry. The slurry was placed in a two-liter flask and heated to about 260° C. to produce gray-black chunks of material which were ground into a powder. The powder was reheated to about 1600° C. in air for about two hours to complete the reaction and distribute the nickel into the lattice structure of the composition NiAl$_2$O$_4$, a nickel spinel. Subsequently the composition was partially reduced with flowing hydrogen at about 650° C. for about 97 hours. X-ray diffraction showed the presence of metallic nickel. The composition is hereinafter described as Ni/NiAl$_2$O$_4$.

A 50 wt. % suspension of Ni/NiAl$_2$O$_4$ in 1% aqueous ammonium alginate solution was ball milled for about 8 hours and then further diluted with an equal volume of water to provide a suitable spraying consistency and decomposable binder for the dried coating. After trial spraying showed that some smooth non-dusting surface coats could be applied to preoxidized cathode surfaces with penetration extending no further than the surface macropores (10–15 μm), the Ni/NiAl$_2$O$_4$ slurry was spray-coated onto the preoxidized nickel oxide cathode.

A test cell was constructed with an electrolyte tile composed of about 48 g of 64 wt. % of a molten carbonate eutectic with the remainder being solid lithium aluminate (LiAlO$_2$) powder particles having a surface area of about 33 m$^2$/g tile was about 4.375 inches×4.375 inches×2 mm. In the assembly of the cell, a perforated sheet metal current collector was laid in the frame of the stainless steel anode housing, followed by the porous Ni/Cr anode, the tile, the pretreated nickel oxide cathode with its spray-coated face adjacent the tile, a second current collector, and the cathode housing member. The assembly with electrical connections to a variable load and fuel and oxidant connections was placed in an oven and heated to about 650° C. under about 10 psi pressure to form an edge-seal at the tile perimeter oversized with respect to the electrodes. Approximately twelve hours were required to form the gas seal. In this conditioning, the extremely reactive nickel metal portion of the Ni/NiAl$_4$O$_4$ thin layer or coating on the cathode was quickly corroded by the molten carbonate and provided a ready source of nickel ion which migrated into the electrolyte tile and formed nickel components on the particulate LiAlO$_2$ surfaces of the tile.

In the test of the cell, a constant current of about 80 ma/cm$^2$ was applied to the cell and its voltage was measured. FIG. 3 includes performance data for several molten carbonate cells including the performance of a series of coated-electrode cells with the baseline performance of an untreated "standard" cell, SQ-20. Tests SQ-21, SQ-23, SQ-24, SQ-27, SQ-28, and SQ-29 were based on cells where lithium aluminate spray-coatings were incorporated on the anode at the anode-tile interface in an effort to reduce hydrogen cross-over during cell operation. Tests for cell SQ-25, the cell of this invention, and six months later, for SQ-32, its duplicate in construction and performance, incorporated the partially-reduced nickel aluminate Ni/NiAl$_2$O$_4$ at the cathode-tile interface, showed essentially equal effectiveness in reducing hydrogen cross-over and in addition were shown to have the earliest rise to plateau performance.

For both cells the voltage reached 0.7 volts within 15–25 hours, and continued at 0.7–0.72 volts for past 200 hours. At the initial time period of 15–25 hours, other cells developed voltages below 0.7 volts and required up to 250 hours to reach their plateau voltages.

This early increase in cell potential was found to be independent of ohmic cell resistance, which for cell SQ-32 was measured by current-interrupt techniques and was found to be constant over the test-life of the cell. The improvement in cell potential rising to a plateau was attributed to a reduction in the polarization processes, particularly to an improvement in oxygen-ion transport, on surfaces of the solid dispersed in the tile body itself, in the regions near the cathode-tile interface. This improvement was further attributed to the improvement in the oxygen ion transport performance of the electrolyte tile apart from the spinel structure and the cathode. Based on the performance of the cell, the spinel structure did not appear to be functioning as an extended cathode nor as the primary electrolyte but as a readily accessible source of nickel for the electrolyte tile by which the nickel could be transferred to the electrolyte tile within a reasonably short time and the oxygen ion transfer of the tile could be enhanced.

EXAMPLE II

Figure 2:
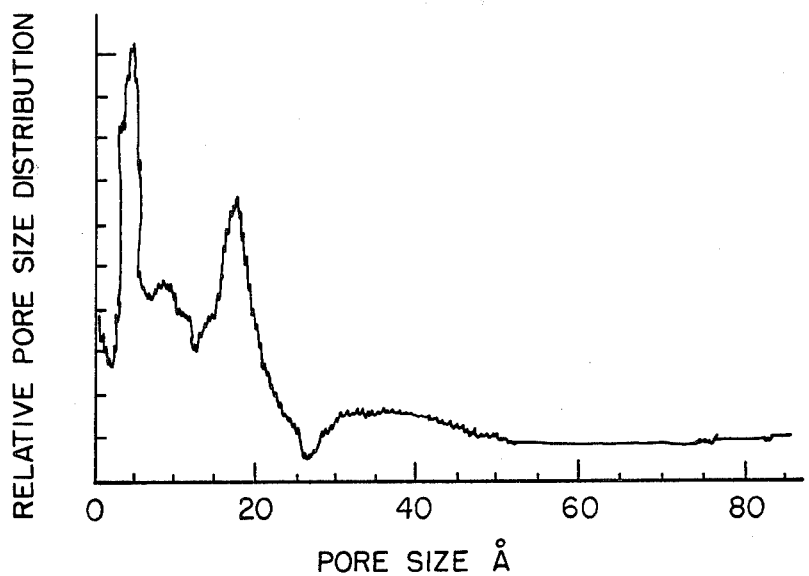
FIG. 2 is a graph of pore size distribution for a sample of manganese dioxide.

In the preparation of a solid electrolyte fuel cell, an epsilon-MnO$_2$ was measured by nitrogen adsorption/desorption isotherm techniques and was found to have a porosity with peak distributions at 8, 20 and 40 Å as shown in FIG. 2 illustrating the pore size distribution of a sample of MnO$_2$ It is ground to a free-flowing powder and formed into a paste with about 10 g. of 50 wt. % Mn(NO$_3$)$_2$ and 65 g. of the MnO$_2$. The paste is spread on an aluminum foil, and spread between spacer-guides to a form about 4 and ⅜ inches×4 and ⅜ inches × 0.07 inches, and overlaid with a second aluminum foil and slowly heated to about 350° C. in a lightly-loaded platten press. The manganous nitrate decomposes to form a (porous) cement of beta-MnO$_2$ which binds the epsilon phase into an electrolyte slab. Repeated impregnation and decomposition in the press yield a gas-impervious electrolyte slab of controlled dimensions.

Electrode attachment is obtained utilizing deadweight loaded quartz plates rather than the platten press, and cementing the anode and the fragile lithiated, preoxidized NiO plaques to either side of the electrolyte slab with aqueous manganous nitrate solution, again employing Al foil release sheets, decomposing the nitrate in a ventilated air oven at 350° C.

The assembly less the quartz plates and aluminum foil pieces is mounted in a conventional molten carbonate fuel cell housing. In the assembly, the electrolyte slab extends beyond the anode and cathode, and combined with the upper and lower housing members, forms seals for the cell. The cell is tested with oxygen and hydrogen at about 500°–600° C. at a constant current of about 200 ma/cm$^2$. A voltage in the order of about 0.5–0.9 V is obtained.

As described herein, the invention provides electrochemical cells with enhanced performance. For the molten carbonate cell, the initial conditioning of the cell is reduced. In a solid electrolyte cell, the combination of small open pores and transition metal oxide in the surrounding composition will permit operation at reduced temperatures.

The embodiments of the invention in which an exclusive property or privilege is claimed are defined as follows:

1. An electrochemical device comprising electrode means and as a solid electrolyte structure, a porous elongated layer having a pair of laterally opposite surfaces and internally composed predominantly of a multiplicity of small, open pores sized below about $1 \times 10^4$ Å, the pores forming a plurality of ion-transfer passages extending laterally between the opposite surfaces for transferring oxygen-ions laterally within the layer, the layer having an electronic insulating composition around said pores composed of a metallic oxide with the formula $$T_a X_b O_c$$

wherein T is a transition metal, X is at least one metal selected from the group consisting of a transition metal, Al, Sn, and an alkali metal, and the integers a, b and c represent the number of atoms to balance the formula, said layer having a density of about 2-5 gm/cc, being essentially gas-tight and stable at temperatures above about 200° C.

2. The solid electrolyte structure of claim 1 wherein said metallic oxide is a manganese oxide.

3. The solid electrolyte structure of claim 1 wherein said metallic oxide is $NiAl_2O_4$.

4. An electrochemical cell comprising an oxygen electrode for generating oxygen ions, means for introducing an oxygen-containing gas to said one electrode, ion transfer means including a solid electrolyte structure and a source of transition metal ions adjoining the one electrode for accepting oxygen ions therefrom, a second electrolyte, a second electrode, and means for inducing an oxygen deficient gas to the second electrode, said structure internally being predominantly composed of a multiplicity of small, open pores forming a plurality of elongated ion-transfer passages for transferring oxygen-ions laterally within the structure, the combination of electrolytes being essentially gas-tight and limiting the passage of oxygen gas through said pores, said structure having a composition around the pores composed of an oxide of at least one multivalent metal having insulating properties with respect to electron transfer and capable of adsorbing and desorbing and readsorbing oxygen ions to serve as an oxygen ion transfer agent.

5. The electrochemical cell of claim 4 wherein said source of transition metal ions is a layer adjacent the oxygen electrode and said second electrolyte is a metal carbonate melting in the range of about 400°-700° C.

6. An electrochemical cell comprising an oxygen electrode for generating oxygen ions, means for introducing an oxygen-containing gas to said one electrode, ion transfer means including a solid electrolyte structure adjoining the one electrode for accepting oxygen ions therefore, a second electrode, and means for introducing a fuel to the second electrode, said structure internally being predominantly composed of a multiplicity of small, open pores sized to permit the passage of oxygen ions but limit the passage of oxygen gas, the pores forming a plurality of elongated ion-transfer passages for transferring oxygen-ions within the layer in a lateral direction away from said one electrode, said structure being essentially gas-tight and having a composition around the pores composed of an oxide of at least one multivalent metal having insulating properties with respect to electron transfer and capable of adsorbing and desorbing and readsorbing oxygen ions to serve as an oxygen ion transfer agent.

7. The device of claim 6 wherein the pores are sized below about $1 \times 10^4$ Å.

8. The device of claim 7 wherein the oxide of the multivalent metal has the formula $$T_a X_b O_c$$

wherein T is a transition metal, X is at least one member selected from the group consisting of the transition metal, Al, Sn, and an alkali metal, and the integers a, b and c represent the number of atoms to balance the formula.

9. The device of claim 8 wherein the metal is manganese.

10. The device of claim 8 wherein the metal is nickel.

11. The device of claim 8 wherein the metal is tin.

12. The device of claim 8 wherein the electrolyte includes a carbonate composition having a melting temperature in the range of about 400°-700° C.

13. The device of claim 8 wherein the electrolyte is essentially said solid electrolyte structure extending laterally between the electrodes.

14. The device of claim 13 wherein said metal is manganese.

* * * * *